US 8,817,077 B2

(12) United States Patent
Urasaki et al.

(10) Patent No.: US 8,817,077 B2
(45) Date of Patent: Aug. 26, 2014

(54) ENDOSCOPE SYSTEM

(71) Applicant: Olympus Medical Systems Corp., Tokyo (JP)

(72) Inventors: Takeshi Urasaki, Tachikawa (JP); Ryu Oshima, Hachioji (JP); Hiroshi Tamai, Tama (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/886,700

(22) Filed: May 3, 2013

(65) Prior Publication Data

US 2013/0300829 A1 Nov. 14, 2013

Related U.S. Application Data

(63) Continuation of application No. PCT/JP2012/070317, filed on Aug. 9, 2012.

(30) Foreign Application Priority Data

Aug. 26, 2011 (JP) ................................. 2011-185130

(51) Int. Cl.
*H04N 13/02* (2006.01)

(52) U.S. Cl.
USPC .......................................................... 348/46

(58) Field of Classification Search
USPC .......................................................... 348/46
See application file for complete search history.

(56) References Cited

U.S. PATENT DOCUMENTS

| 5,258,834 | A | * | 11/1993 | Tsuji et al. ...................... 348/71 |
| 2009/0290016 | A1 | | 11/2009 | Suda |
| 2010/0160728 | A1 | | 6/2010 | Yoshie |

FOREIGN PATENT DOCUMENTS

| EP | 2 151 182 A1 | 2/2010 |
| JP | 2000-019426 A | 1/2000 |
| JP | 2003-038422 A | 2/2003 |
| JP | 2003-038432 A | 2/2003 |
| JP | 2004-222937 A | 8/2004 |
| JP | 2006-288831 A | 10/2006 |
| JP | 2009-279060 A | 12/2009 |
| JP | 2010-035874 A | 2/2010 |

* cited by examiner

*Primary Examiner* — Dave Czekaj
*Assistant Examiner* — Leron Beck
(74) *Attorney, Agent, or Firm* — Scully, Scott, Murphy & Presser, P.C.

(57) ABSTRACT

An endoscope system includes processors, and settings in the processors are at least partially in common. And a setting content in a processor determined to have a higher priority is transmitted to a processor determined to have a lower priority, based on a predetermined operation, and the processor changes a setting content that is in common with a setting content in the processor among the received setting contents.

5 Claims, 8 Drawing Sheets

US 8,817,077 B2

ENDOSCOPE SYSTEM

CROSS REFERENCE TO RELATED APPLICATION

This application is a continuation application of PCT/JP2012/070317 filed on Aug. 9, 2012 and claims benefit of Japanese Application No. 2011-185130 filed in Japan on Aug. 26, 2011, the entire contents of which are incorporated herein by this reference.

BACKGROUND OF THE INVENTION

1. Field of the Invention

The present invention relates to an endoscope system, and specifically relates to an endoscope system including two medical devices, settings in the medical devices being partially in common

2. Description of the Related Art

Conventionally, medical device systems such as endoscope systems have widely been used. For example, there are various types of endoscope systems such as stereoscopic endoscope systems that enable stereoscopic observation of an object, frame-sequential-type endoscope systems and simultaneous-type endoscope systems.

For example, as disclosed in Japanese Patent Application Laid-Open Publication No. 2004-222937, a stereoscopic endoscope system is constructed by combining two processors that process two endoscopic images, in order to combine two endoscopic images to generate an image to be observed.

Also, in facilities such as hospitals, there coexist a plurality of processors for endoscopes, and thus, such processors may be used in various combinations. For example, where a simultaneous-type endoscope system is constructed, the system is constructed by connecting peripheral devices such as a monitor and a light source apparatus to a simultaneous-type processor. Also, where a frame-sequential-type endoscope system is constructed, the system is constructed by connecting peripheral devices such as a monitor and a light source apparatus to a frame-sequential-type processor.

SUMMARY OF THE INVENTION

An endoscope system according to an aspect of the present invention provides an endoscope system in which a first processor and a second processor are connected in such a manner that the first processor and the second processor can communicate with each other, the endoscope system including: a first image pickup device that picks up an image of an inside of a body cavity and outputs a first image pickup signal; a first processor that processes the first image pickup signal from the first image pickup device and outputs a first image signal, and transmits a first setting content that is set, via communication; a second image pickup device that picks up an image of the inside of the body cavity and outputs a second image pickup signal; a second processor that processes the second image pickup signal from the second image pickup device and outputs a second image signal, and changes a common setting content based on the setting content received from the first processor via communication, the second processor having a priority determined to be lower than that of the first processor; a three-dimensional image generation apparatus that generates a three-dimensional image from the first image signal and the second image signal; and an operation device via which an operational instruction for the first processor is inputted, wherein upon an input of an operational instruction for still image display via the operation device, the first processor makes a setting for or provides an instruction to the three-dimensional image generation apparatus so as to output only the first image signal.

DETAILED DESCRIPTION OF THE PREFERRED EMBODIMENTS

Embodiments of the present invention will be described below with reference to the drawings.

(First Embodiment)
(Configuration)

Figure 1:
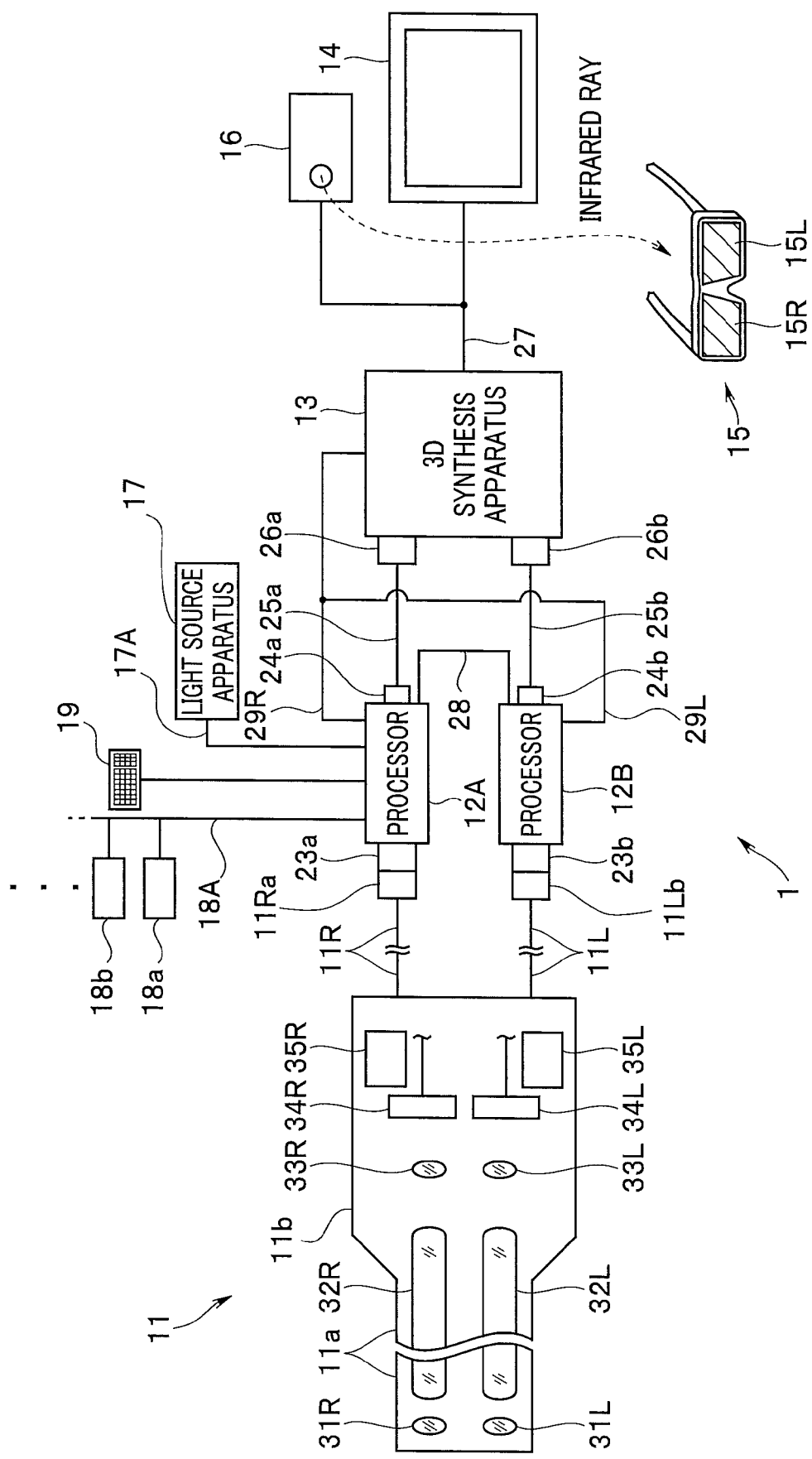
FIG. 1 is a diagram illustrating an internal configuration of a stereoscopic endoscope according to a first embodiment of the present invention, and a configuration of a stereoscopic endoscope system, which includes a connection to liquid-crystal shutter glasses.

FIG. 1 is a diagram illustrating a configuration of a stereoscopic endoscope system according to the present embodiment, which includes an internal configuration of a stereoscopic endoscope and a connection to liquid-crystal shutter glasses. As illustrated in FIG. 1, a stereoscopic endoscope system 1 according to the present embodiment is a medical device system mainly including a stereoscopic endoscope 11, two processors 12A and 12B, a 3D synthesis apparatus 13 and a monitor 14. In the present embodiment, the two processors 12A and 12B, which are medical devices, are used in the stereoscopic endoscope system.

The stereoscopic endoscope 11 includes an elongated insertion portion 11a and an operation portion 11b, and also includes two optical systems that provide a parallax difference on the distal end side of the insertion portion 11a, the optical systems conveying respective optical images to two image pickup apparatuses such as CCDs that pick up images of the inside of a body cavity and outputting image pickup signals from the respective image pickup apparatuses. The two processors 12A and 12B perform signal processing of respective image pickup signals outputted from the two image pickup apparatuses in the stereoscopic endoscope 11 to output video signals. The 3D synthesis apparatus 13 is a scan converter that converts scanning of the video signals from the processors 12A and 12B and outputs the video signals while switching between the video signals. The monitor 14 is an image display apparatus that alternately displays left and right images upon an input of the video signals outputted from the 3D synthesis apparatus 13.

Also, the stereoscopic endoscope system 1 further includes liquid-crystal shutter glasses 15 for viewing a display screen of the monitor 14 and an opening/closing control apparatus 16 that controls opening/closing of shutters in the liquid-crystal shutter glasses 15.

As described later, a light source apparatus 17 is connected to the processor 12A, which is a master processor, via a cable 17A. A plurality of other peripheral devices 18a, 18b, etc., are connected to the processor 12A, which is a master processor (hereinafter also referred to as master device), via a connection cable 18A. Examples of the peripheral devices include a gas feeding apparatus, a digital image recording apparatus (DVR), a printer and a filing apparatus.

A keyboard 19 is connected to the processor 12A. Although not illustrated, a foot switch is also connected to the processor 12A. Where the system operates as a stereoscopic endoscope system, operation devices such as the keyboard 19 and the foot switch connected to the processor 12A, which is a master device, are used.

Figure 2:
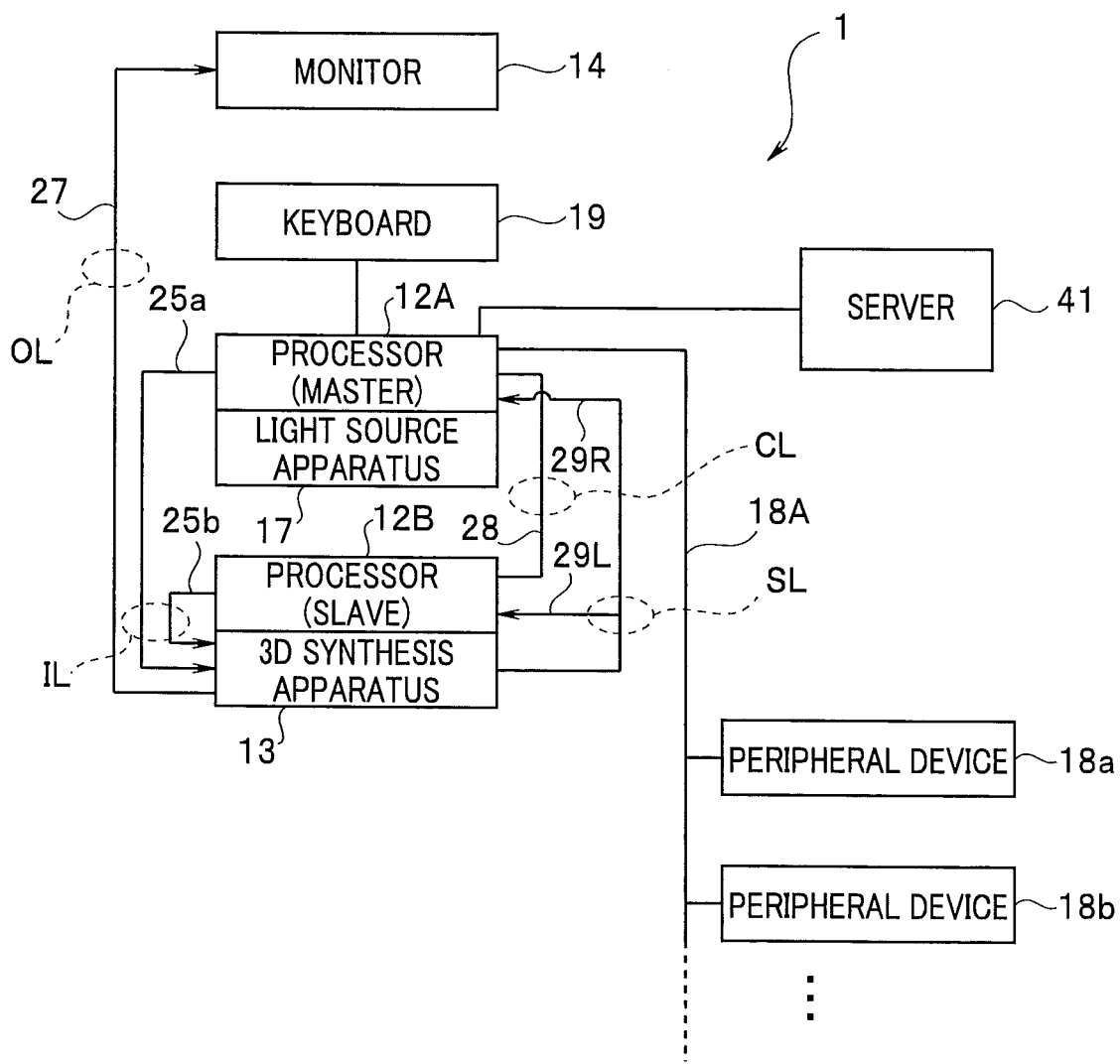
FIG. 2 is a block configuration diagram of an endoscope system 1 according to the first embodiment of the present invention, which indicates a connection relationship between processors 12A and 12B and other apparatuses excluding a stereoscopic endoscope 11 and liquid-crystal shutter glasses 15.

Furthermore, the processor 12A is connected with a server 41 (FIG. 2). The server 41 is, for example, a server in a hospital and includes a storage apparatus having a storage capacity allowing various data to be stored therein.

The stereoscopic endoscope 11 is configured in such a manner that camera connectors 11Ra and 11Lb of camera cables 11R and 11L respectively extending out from the operation portion 11b are connected to respective receptacles 23a and 23b of the processors 12A and 12B.

Also, the processor 12A is configured in such a manner that a signal cable 25a extending out from a connector 24a is connectable to a signal connector 26a or 26b of the 3D synthesis apparatus 13. On the other hand, the processor 12B is also configured in such a manner that a signal cable 25b extending out from a connector 24b is connectable to a signal connector 26a or 26b of the 3D synthesis apparatus 13. Here, the signal cable 25a is connected to the signal connector 26a, and the signal cable 25b is connected to the signal connector 26b.

The present embodiment is configured so that each of the camera connectors 11Ra and 11Lb of the camera cables 11R and 11L may be connected to either of receptacles 23a and 23b of the processors 12A and 12B and the processors 12A and 12B may be connected to either of the signal connectors 26a and 26b of the 3D synthesis apparatus 13.

Also, the 3D synthesis apparatus 13 is connected to the monitor 14 via a monitor cable 27. Furthermore, a branch cable of the monitor cable 27 for the 3D synthesis apparatus 13 is connected to the opening/closing control apparatus 16.

The opening/closing control apparatus 16 is configured so that a user can observe two images alternately displayed on the monitor 14 as an object image having a three-dimensional appearance by closing/opening the shutters in the liquid-crystal shutter glasses 15.

Also, the processors 12A and 12B are connected via a signal cable 28 so that the processors 12A and 12B can be synchronized with each other.

Furthermore, in order to receive respective synchronization signals for images, the processors 12A and 12B are connected to the 3D synthesis apparatus 13 via synchronization cables 29R and 29L.

For each of the processors, whether genlock, that is, synchronization of a horizontal synchronization signal and a vertical synchronization signal for a video signal with an external signal, is enabled or disabled can be set. Accordingly, when a user links the two processors 12A and 12B to use the two processors 12A and 12B as a stereoscopic endoscope system, genlock is enabled, and when a user uses each of the processors in stand-alone mode, genlock is disabled.

Next, a specific configuration of the stereoscopic endoscope system 1 will be described.

The stereoscopic endoscope 11 includes a right optical system 31R that captures a right optical image of an object and a left optical system 31L that captures a left optical image of the object on the distal end side of the insertion portion 11a.

At a position where an image is formed in the right optical system 31R, an incident end face of a right image transmission optical system 32R such as a relay lens is arranged and a right optical image of an object falls on the incident end face and is transmitted to the rear end side of the insertion portion 11a. Then, on an exit end face of the right image transmission optical system 32R, a right image forming optical system 33R and a CCD (charge-coupled device) 34R, which is a right image pickup apparatus, are arranged so that the right optical image of the object is formed on an image pickup surface of the CCD 34R.

On the other hand, a configuration similar to that for the right is provided for the left, at a position where an image is formed in the left optical system 31L, an incident end face of a left image transmission optical system 32L is arranged and a left optical image of an object falls on the incident end face and is transmitted to the rear end side of the insertion portion 11a. Then, on an exit face of the left image transmission optical system 32L, a left image forming optical system 33L and a CCD 34L, which is a left image pickup apparatus, are arranged so that the left optical image of the object is formed on an image pickup surface of the CCD 34L.

Accordingly, the right optical system 31R, the right image transmission optical system 32R, the right image forming optical system 33R and the CCD 34R provide an endoscope including an image pickup apparatus that picks up an image of the inside of a body cavity and outputs an image pickup signal, and the left optical system 31L, the left image transmission optical system 32L, the left image forming optical system 33L and the CCD 34L also provide another endoscope including an image pickup apparatus that picks up an image of the inside of a body cavity and outputs an image pickup signal.

Although not illustrated, an illumination optical system is disposed in the stereoscopic endoscope 11 so that illuminating light from the light source apparatus 17 is transferred to a distal end portion to illuminate an object.

Also, the stereoscopic endoscope 11 includes an ID memory 35R that outputs a right identification signal indicating that "the relevant image is one picked up by the CCD 34R, which is a right image pickup apparatus", as an identification signal generating section, and an ID memory 35L that outputs a left identification signal indicating that "the relevant image is one picked up by the CCD 34L, which is a left image pickup apparatus" as an identification signal generating section, in the inside thereof.

In the present embodiment, as described later, the ID memory 35R and the ID memory 35L are configured so as to output a low/high signal as a right/left identification signal.

Furthermore, in each of the ID memory 35R and the ID memory 35L, identification information, that is, ID information for the endoscope is stored.

The ID memories 35R and 35L may be incorporated in the camera connectors 11Ra and 11Lb, respectively. Also, left/right discrimination and endoscope identification may be performed using pull-up resistors instead of the ID memories.

In the stereoscopic endoscope 11, upon each of the camera connectors 11Ra and 11Lb being connected to the receptacle 23a or 23b of the processor 12A or the processor 12B, the CCD 34R and 34L are driven by control of non-illustrated respective drive circuits in the processors 12A and 12B via signal wires disposed through the camera cables 11R and 11L. Then, each of the driven CCDs 34R and 34L photoelectrically converts a formed optical image of an object and accumulates the resulting charge.

Then, the charges accumulated in the CCDs 34R and 34L are read in the respective drive circuits as image pickup signals and outputted to video signal conversion circuits in the processors 12A and 12B via the signal wires disposed through the camera cables 11R and 11L, respectively, and converted into standard video signals in the video signal conversion circuit and transferred to the 3D synthesis apparatus 13.

The processor 12A provides a processor, which is a medical device, the processor being connected with a first endoscope including, e.g., the CCD 34R and processing an image pickup signal from the endoscope to output an image signal, and the processor 12B provides a processor, which is a medical device, the processor being connected with a second endoscope including, e.g., the CCD 34L and processing an image pickup signal from the endoscope to output an image signal.

Also, the right identification signal in the ID memory 35R is transmitted via the signal wire disposed through the camera cable 11R, and transferred to the 3D synthesis apparatus 13 via the processor 12A or the 12B. On the other hand, the left identification signal in the ID memory 35L is also transmitted via the signal wire disposed through the camera cable 11L and transferred to the 3D synthesis apparatus 13 via the processor 12A or 12B.

The 3D synthesis apparatus 13 provides a three-dimensional image generation apparatus that generates a three-dimensional image from two image signals.

The 3D synthesis apparatus 13 outputs video signals from the processors 12A and 12B to the monitor 14 while switching between the video signals. Then, the monitor 14 alternately displays left and right video images on the display screen based on the inputted video signals.

Here, the opening/closing control apparatus 16 includes a non-illustrated infrared transmitter. On the other hand, the liquid-crystal shutter glasses 15 include a non-illustrated infrared receiver so that switching for opening/closing of liquid-crystal shutters 15R and 15L is performed by means of infrared communication with the opening/closing control apparatus 16.

In the liquid-crystal shutter glasses 15, during a video image for a right eye being displayed on the monitor 14 under the control of the opening/closing control apparatus 16, the right liquid-crystal shutter 15R is opened and the left liquid-crystal shutter 15L is closed, whereby the video image on the monitor 14 can be observed by a right eye alone.

On the other hand, contrarily, in the liquid-crystal shutter glasses 15, during a video image for a left eye being displayed on the monitor 14, the left liquid-crystal shutter 15L is opened and the right eye liquid-crystal shutter 15R is closed, whereby the video image on the monitor 14 can be observed by a left eye alone.

FIG. 2 is a block configuration diagram of the endoscope system 1, which indicates a relationship of connection between the processors 12A and 12B and other apparatuses excluding the stereoscopic endoscope 11 and the liquid-crystal shutter glasses 15.

The signal cable 28 connecting the processors 12A and 12B includes a control-related signal wire CL. The signal cables 25a and 25b connecting the processors 12A and 12B to the 3D synthesis apparatus 13 includes respective video signal-related signal wires IL. The monitor cable 27A connecting the 3D synthesis apparatus 13 and the monitor 14 includes a 3D image-related signal wire OL. The synchronization cables 29R and 29L that transmit respective synchronization signals from the 3D synthesis apparatus 13 to the processors 12A and 12B include respective signal wires SL for synchronization.

As described later, here, the processor 12A is set as a master device and the processor 12B is set as a slave device, and settings in the slave device are automatically made.

On the monitor 14, not only a video image of an object may stereoscopically be displayed but also a menu screen may be displayed. The menu screen is used for, for example, a user to make various settings. The menu screen can be displayed on the monitor 14 by combining video signals from the two processors 12A and 12B; however, the displayed menu screen do not have to be stereoscopically displayed and may be what is called 2D display.

Therefore, the master device (here, the processor 12A) can make a setting in or provide an instruction to the 3D synthesis apparatus 13 so that only a video signal from the master device is outputted as a video output to the monitor 14 when the menu screen is displayed.

In other words, a user can make a setting so that the 3D synthesis apparatus 13 outputs only a video signal from the master device to the monitor 14 at the time of display of the menu screen. Therefore, when a user makes such setting in or provides such instruction to the master device, the 3D synthesis apparatus 13 outputs only a video signal from the master device to the monitor 14 when the menu screen is displayed.

Also, a still image may be displayed on the monitor 14. For example, when a user presses a freeze button in the stereoscopic endoscope 11, a still image can be obtained and displayed on the monitor 14. Video signals from the two processors 12A and 12B are combined and displayed on the monitor 14. However, if there is a difference between timings of obtainment of respective still images by the two processors 12A and 12B, the combined and displayed still image may be displayed in an unsteady state (that is, flickering state).

Therefore, the master device (here, the processor 12A) can make a setting in or provides an instruction to the 3D synthesis apparatus 13 so as to, when a still image is displayed, output only a video signal from the master device as a video output to the monitor 14.

In other words, a user can make a setting so that the 3D synthesis apparatus 13 outputs only a video signal from the master device to the monitor 14 at the time of display of a still image. Therefore, when a user makes such setting or provides such instruction to the master device, the 3D synthesis apparatus 13 outputs only a video signal from the master device to the monitor 14 when a still image is displayed.

Also, where the two processors 12A and 12B are linked for use in a stereoscopic endoscope system, processing for synchronizing clocks in the two processors 12A and 12B, that is, setting the respective times; however, since there may be a difference in time between the two processors 12A and 12B, clock display on the screen of the monitor 14 may be displayed in an unsteady manner. Therefore, for clock display, the master device (here, the processor 12A) can make a setting in or provide an instruction to the 3D synthesis apparatus 13 so as to output only clock display of the master device.

Still furthermore, where the system is used as a stereoscopic endoscope system, since a user uses the liquid-crystal shutter glasses 15 to see the monitor 14, the screen appears darker to the user compared to a case where the user see 2D display on the monitor 14 without using the liquid-crystal shutter glasses 15. Therefore, where the system is used as a stereoscopic endoscope system, the master device (here, the processor 12A) outputs an adjustment signal for changing a setting so as to increase a brightness of the monitor 14 to the monitor 14.

Furthermore, where the system is used as a stereoscopic endoscope system, a user performs an operation of the master device and thus, the slave device (here, the processor 12B) turns off lamps, for example, LED (light-emitting diode) lamps on an operation panel thereof. Thus, only LED lamps on an operation panel of the master device are on and the LED lamps of the operation panel of the slave device are off, which prevents the user from operating the slave device by mistake.

Note that where there is a peripheral device connected to the slave processor, the master processor does not perform control of the peripheral device connected to the slave processor.

(Operation)

Figure 3:
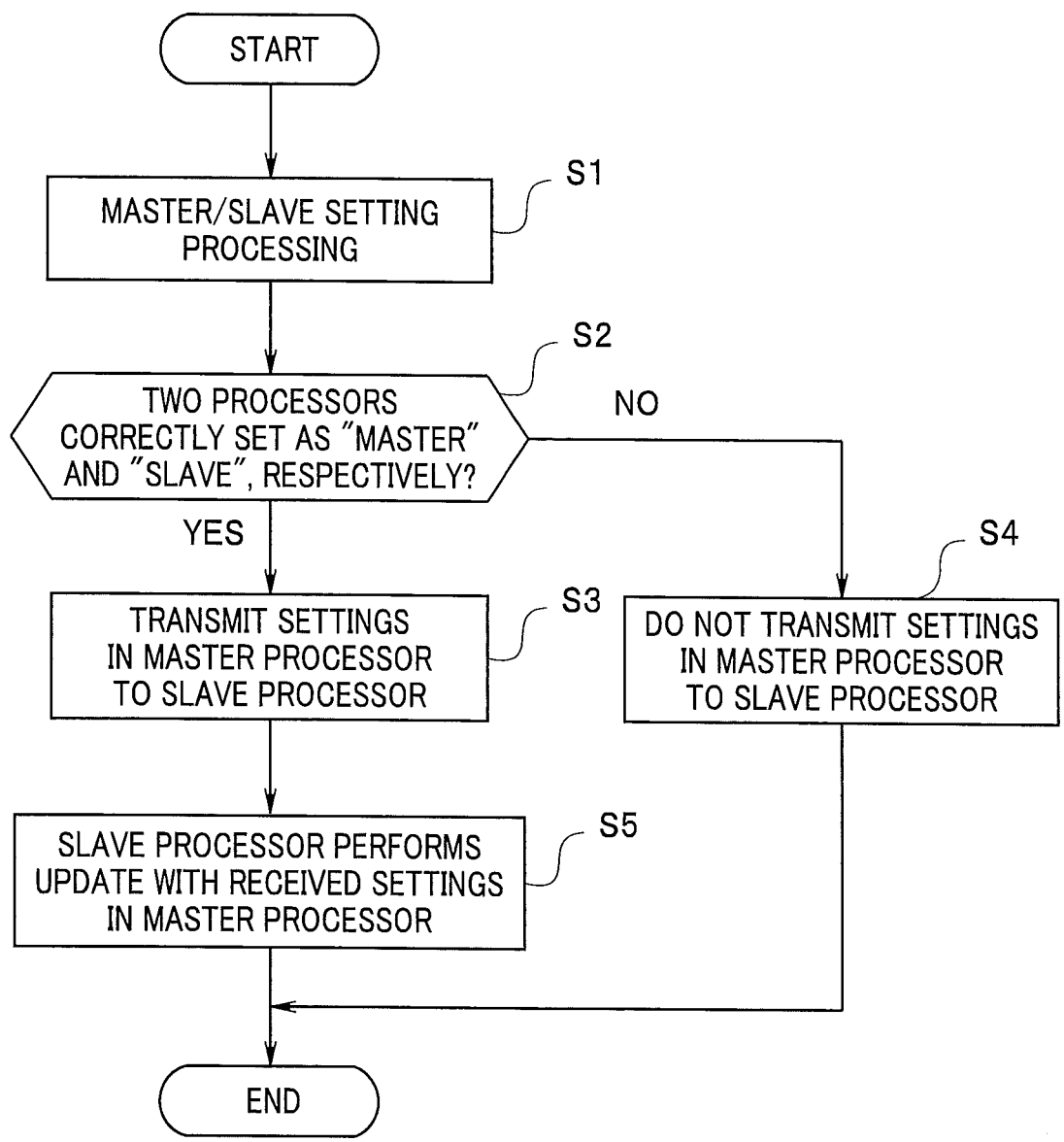
FIG. 3 is a flowchart illustrating an example of processing for settings in the endoscope system 1 according to the first embodiment of the present invention.

FIG. 3 is a flowchart illustrating an example of setting processing for the endoscope system 1.

First, after the processors 12A and 12B and the other apparatuses are connected as illustrated in FIGS. 1 and 2, master/slave setting processing for making a setting to determine which processor is a master device and which processor is a slave device is performed (S1). Each processor has a master/slave setting function. Here, the processor 12A is a master device and the processor 12B is a slave device and thus master/slave setting is performed for each processor on a setting screen of the processor.

Figure 4:
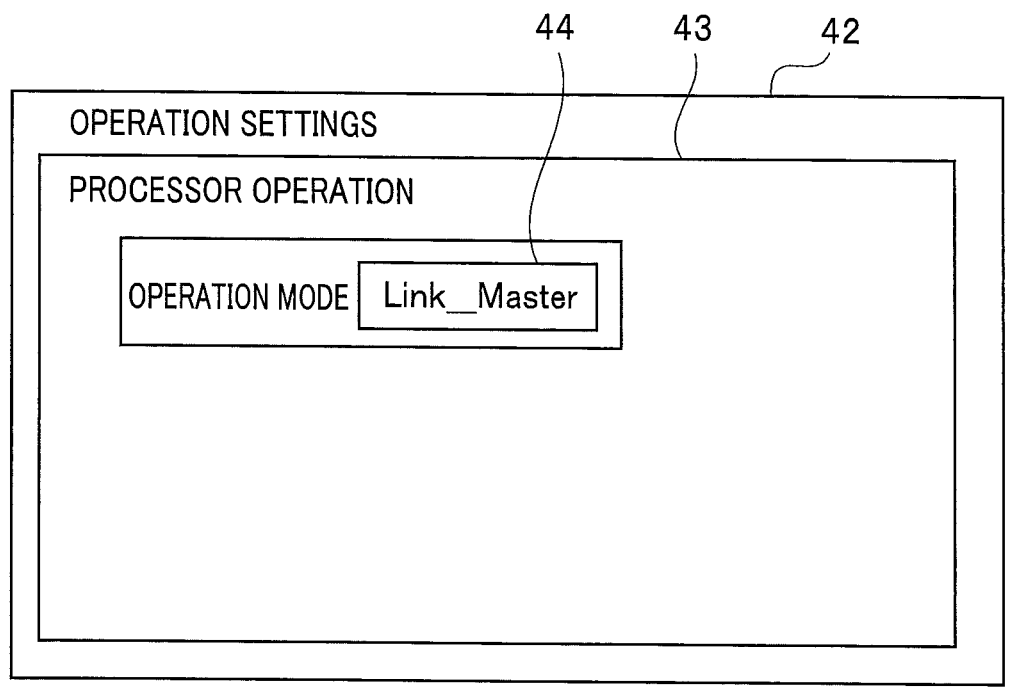
FIG. 4 is a diagram illustrating am example of a master/slave setting screen for each processor, according to the first embodiment of the present invention.

FIG. 4 is a diagram illustrating an example of the master/slave setting screen of each processor. FIG. 4 illustrates a setting window displayed on the screen of the monitor 14 as a result of, for example, a predetermined operation being performed on the processor 12A. A window 42 displayed on the screen of the monitor 14 is a window for setting various operations, and in FIG. 4, in a frame 43 for settings for processor operations from among various operations, a setting field 44 for setting an operation mode is displayed.

In order to set the processor 12A as a master device, a user of the endoscope system 1 inputs "Link_Master" in the setting field 44 or a selected mode is displayed on the screen in FIG. 4. As a result of recording the setting in FIG. 4 in an internal memory such as a flush memory in the processor 12A, the processor 12A is set as "master" and the content of the setting is stored.

Although not illustrated, for the processor 12B, also, the window 42 in FIG. 4 is displayed on the screen of the monitor 14 and then the user sets the processor 12B as "slave". For example, in the setting field 44, "Link_Slave" is inputted or selected, and registered in the processor 12B.

The processor 12A set as "master" has a priority higher than that of the processor 12B set as "slave", and the processor 12B set as "slave" has a priority higher than that of the processor 12A set as "master". In other words, as a result of processing in 51, the processor 12A is determined to have a higher priority and the processor 12B is determined to have a lower priority.

Also, in the operation mode setting, if a processor is used alone, in the setting field 44, "Stand_Alone" is inputted or selected, and registered in the processor.

Note that the master/slave setting may be performed via, e.g., the operation panel of each processor or a dedicated selection switch.

After the master/slave setting has been made for each of the two processors 12A and 12B, the processor that functions as a master device determines whether or not the two processors 12A and 12B are correctly set as "master" and "slave", respectively (S2). Here, the processor 12A set as "master" performs processing for the determination.

The determination is made by the processor 12A communicating with the processor 12B to acquire information on an operation mode of the processor 12B via the signal cable 28, which includes the control wire CL, and comparing the operation mode with an operation mode of the processor 12A itself.

If the two processors are correctly set as "master" and "slave", respectively, that is, the operation mode of the processor 12B is set as "slave" and the operation mode of the processor 12A is set as "master" (S2: YES), the master processor transmits setting information pieces of its own to the slave processor (S3). Here, the processor 12A transmits the setting information pieces of its own to the processor 12B.

The setting information pieces transmitted in S3 are setting information pieces relating to image quality settings such as color tone and video output settings such as aspect ratio. If the stereoscopic endoscope system 1 includes two processors 12A and 12B, it is necessary that settings in the processors 12A and 12B be at least partially in common.

In other words, the processing in S3 provides a transmission section that transmits setting contents in the processor 12A, which is a medical device determined to have a higher priority based on the predetermined operation in S1 to the processor 12B, which is a medical device determined to have a lower priority based on the predetermined operation in S1.

If the two processors are not correctly set as "master" and "slave", respectively, for example, if the operation mode of the processor 12B and the operation mode of the processor 12A itself are both set as "master" (S2: NO), the master processor does not transmit the setting information pieces of its own to the slave processor (S4) and terminates the processing.

When the setting information pieces of the master processor have been transmitted to the slave processor (S3), the slave processor updates setting information pieces of its own with the received setting information pieces of the master processor (S5). Here, the processor 12B updates the setting information pieces of its own with the corresponding setting information pieces from the processor 12A.

Note that here, although the slave processor updates the setting information pieces of its own for all of the setting information pieces received from the master processor, it is possible that the master processor transmits setting information pieces including an information piece for which an update is needed in the slave processor and the slave processor extracts only the information piece for which an update is needed from the received setting information pieces and performs a setting information update. In other words, the slave processor may select or extract a setting information piece in common with the master processor from the received setting information pieces to perform an update with only the setting in common with the setting content in the slave processor itself.

In other words, the processing in S5 provides a setting content changing section that changes a setting that is in common with a setting content in the slave processor from among received setting contents in the master processor (for example, settings such as an image quality setting and/or a video output setting) to the received setting content in the master processor, in the slave processor. Note that it is also possible to consider the processing in S3 and S5 as providing a setting content changing section that transmits a setting content in the master processor to a slave processor and changes a setting content in the slave processor based on the received setting content in the master processor.

Then, after the processing in S5, the slave processor turns off the LED lamps on the operation panel thereof.

When the priority confirmation and the setting update above have been performed, the master processor confirms the stereoscopic endoscope 11 and the 3D synthesis apparatus 13 connected thereto, for correct operation of the stereoscopic endoscope system.

More specifically, the processor 12A, which is a master processor, confirms if the right and left sides of the connected endoscope are correct, if IDs of the connected endoscopes are the same, and also if a 3D synthesis apparatus is connected. After the confirmation, the connected stereoscopic endoscope is connected with the left and right sides thereof not reversed, two stereoscopic endoscopes are not connected, and a 3D synthesis apparatus is correctly connected, enabling a user to correctly have stereoscopic vision.

In other words, after the conformation of the connected stereoscopic endoscope and the connected 3D synthesis apparatus as described above, the processor 12A and the processor 12B can provide a function as a stereoscopic endoscope system in cooperation with each other.

Then, when the master processor operates as a stereoscopic endoscope system in cooperation with the slave processor, the master processor performs control of the monitor, the keyboard and various peripheral devices.

As described above, the above-described embodiment eliminates the need for making settings common to two processors when a stereoscopic endoscope system is constructed using the two processors.

(Second Embodiment)

Although the first embodiment provides an example where two processors are used in cooperation with each other in a stereoscopic endoscope system, a second embodiment provides an example where both of a simultaneous-type endoscope system and a frame-sequential-type endoscope system can be used using two processors and peripheral devices are shared by the systems.

(Configuration)

Figure 5:
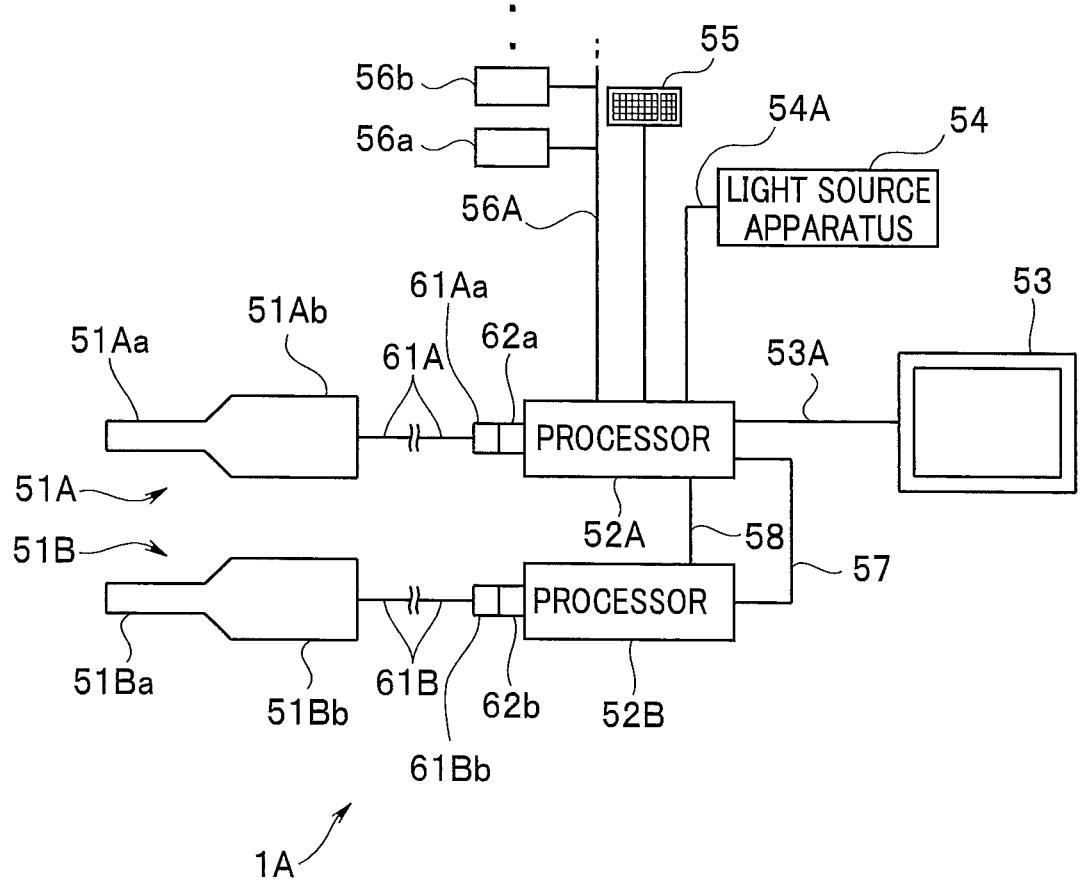
FIG. 5 is a diagram illustrating a configuration of an endoscope system according to a second embodiment of the present invention.

FIG. 5 is a diagram illustrating a configuration of an endoscope system according to the present embodiment. As illustrated in FIG. 5, an endoscope system 1A according to the present embodiment is a medical device system mainly including two endoscopes 51A and 51B, two processors 52A and 52B, a monitor 53, a light source apparatus 54 and a keyboard 55. Peripheral devices such as the monitor 53 are connected to the processor 52A determined as a master device as described later.

The endoscopes 51A and 51B include elongated insertion portions 51Aa and 51Ba and operation portions 51Ab and 51Bb, respectively, and each include an optical system on the distal end side of the respective insertion portion, and transmit an optical image to a shooting apparatus such as a CCD that picks up an image of the inside of a body cavity and output an image pickup signal from the image pickup apparatus. The endoscope 51A is an endoscope connectable to the processor 52A, and the endoscope 51B is an endoscope connectable to the processor 52B. The processor 52A performs signal processing of the image pickup signal outputted from the image pickup apparatus in the endoscope 51A connected thereto to output a video signal, which is an image signal. The processor 52B performs signal processing of an image pickup signal outputted from the image pickup apparatus in the endoscope 51B connected thereto to output a video signal, which is an image signal. The monitor 53 is an image display apparatus connected to the processor 52A, the image display apparatus displaying an image upon an input of a video signal.

As described later, the processor 52A can detect an endoscope connection state in the processor 52B by means of communication with the processor 52B. Where the endoscope 51A is connected to the processor 52A and the endoscope 51B is not connected to the processor 52B, the processor 52A makes circuit connections with the peripheral devices to be connected to the processor 52A. Also, if the endoscope 51A is not connected to the processor 52A and the endoscope 51B is connected to the processor 52B, the processor 52A internally switches the circuit connections with the peripheral devices to a connection with the processor 52B.

A configuration will be described assuming that the processor 52A is set as a master processor and the processor 52B is set as a slave processor. The keyboard 55 is connected to the processor 52A, which is a master processor.

The light source apparatus 54 is an apparatus that supplies illuminating light to the endoscopes 51A and 51B and also is what is called universal light source apparatus that is compatible with both the simultaneous method and the frame-sequential method, the light source apparatus 54 being connected to the processor 52A via a signal cable 54A.

Also, a plurality of other peripheral devices 56a, 56b, and the like, are connected to the processor 52A, which is a master processor, via a connection cable 56A. Examples of the peripheral device include, e.g., a gas feeding apparatus, a digital image recording apparatus (DVR), a printer and a filing apparatus.

Figure 6:
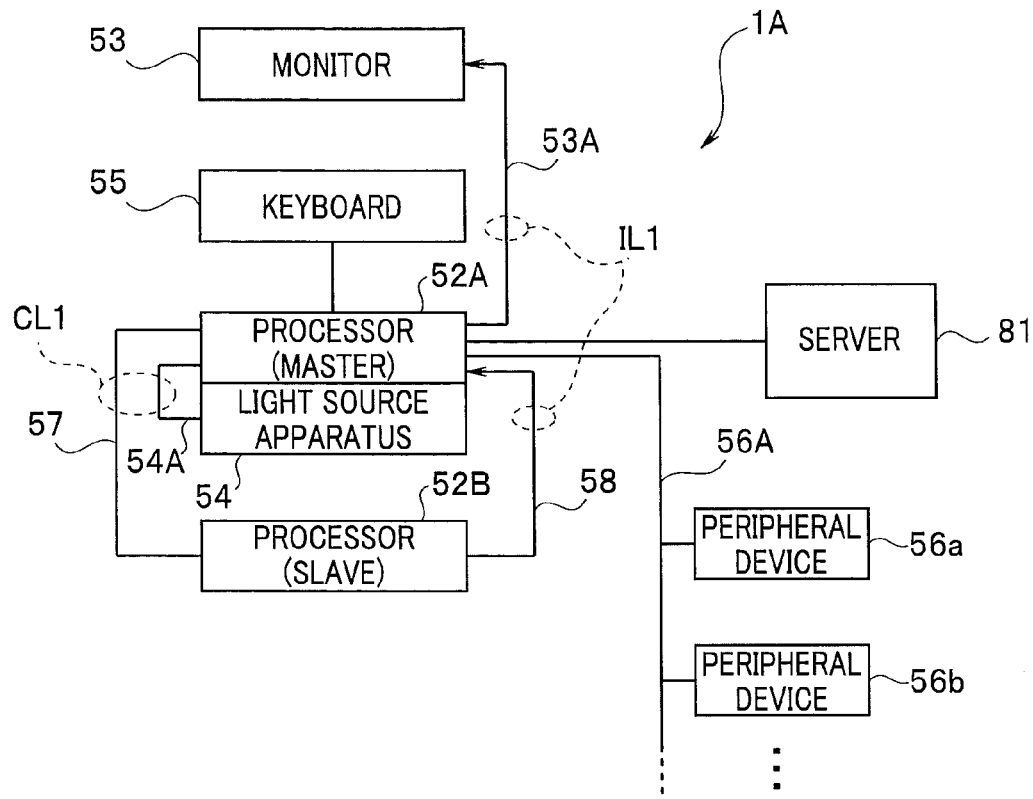
FIG. 6 is a block configuration diagram of an endoscope system 1A according to the second embodiment of the present invention, which indicates a connection relationship between processors 52A and 52B and other apparatuses excluding endoscopes 51A and 51B.

Furthermore, the processor 52A is connected to a server 81 (FIG. 6). The server 81 is, for example, a server in a hospital, and includes a storage apparatus having a storage capacity allowing various data to be stored therein.

Camera connectors 61Aa and 61Bb of camera cables 61A and 61B extending out from operation portions 51Ab and 51Bb of the endoscopes 51A and 51B are connected to receptacles 62a and 62b of the processors 52A and 52B, respectively. The endoscope 51A is an endoscope used for a simultaneous-type endoscope system, and the endoscope 51B is an endoscope used for a frame-sequential-type endoscope system.

The processor 52A is a simultaneous-type processor and the processor 52B is a frame-sequential-type processor.

Also, the processors 52A and 52B, which are medical devices, are mutually connected via signal cables 57 and 58. The monitor 53 and the processor 52A are connected via a signal cable 53A.

FIG. 6 is a block configuration diagram of the endoscope system 1A, which indicates a connection relationship between the processors 52A and 52B and other apparatuses excluding the endoscopes 51A and 51B.

The signal cable 57 for communication, which connects the processors 52A and 52B, and the signal cable 54A connecting the processor 52A and the light source apparatus 54 each include a control-related signal wire CL1. The signal cable 53A connecting the processor 52A and the monitor 53 and the signal cable 58 connecting the processor 52A and the processor 52B each include a video signal-related signal wire IL1. A video output terminal of the processor 52B and an external input terminal of the processor 52A are connected via the signal cable 58.

In the present embodiment, the processor 52A is set as a master device and the processor 52B is set as a slave device, and settings in the slave device are automatically made.

When a system with the configuration illustrated in FIGS. 5 and 6 is used as a simultaneous-type endoscope system, a user powers on the processor 52A and further powers on the light source apparatus 54 and the other peripheral devices, and connects the endoscope 51A to the processor 52A, whereby the system can be used as a simultaneous-type endoscope system. Upon the processor 52A being powered on, the processor 52A can detect that the endoscope 51A is connected thereto, the system including the processor 52A operates as a simultaneous-type endoscope system.

Also, when the system with the configuration illustrated in FIGS. 5 and 6 is used as a frame-sequential-type endoscope system, a user powers on the processor 52A and 52B and further powers on the light source apparatus 54 and the other peripheral devices, and connects the endoscope 51B to the processor 52B, whereby the system can be used as a frame-sequential-type endoscope system. Upon the processor 52A being powered on, the processor 52A can detect that the endoscope 51A is not connected thereto, and the processor 52A can obtain information regarding whether or not the endoscope 51B is connected to the processor 52B by means of communication with the processor 52B via the signal cable 57, and thus, the processor 52A switches the connections with various peripheral devices so that such peripheral devices are connected with the processor 52B, and the system including the processor 52B operates as a frame-sequential-type endoscope system.

Note that when the endoscope 51A is connected to the processor 52A and the endoscope 51B is connected to the processor 52B, the processor 52A switches the circuit connections with the peripheral devices so that the peripheral devices are connected to the processor 52A.

The light source apparatus 54 is controlled by a light source control signal from the processor 52A in the case of a simultaneous-type system, and by a light source control signal from the processor 52B in the case of a frame-sequential-type system. However, since the light source apparatus 54 is connected only to the processor 52A, which is a master processor, a changeover switch for light source control signal is provided in the master processor 52A so that the light source apparatus 54 can receive a control signal from the processor 52B.

Figure 7:
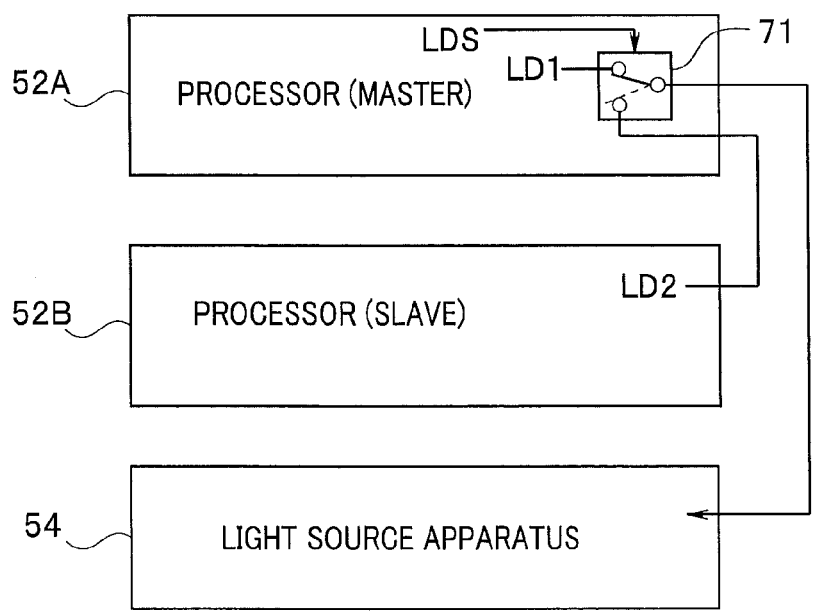
FIG. 7 is a diagram for describing a changeover switch for a light source control signal according to the second embodiment of the present invention.

FIG. 7 is a diagram for describing a changeover switch for light source control signal. The processor 52A, which is a master processor, includes a changeover switch 71, and the changeover switch 71 is a switch with two inputs and one output. The changeover switch 71 provides a connection such that a light source control signal LD1 from the processor 52A to the light source apparatus 54 is inputted to one of two input terminals of the changeover switch 71, and a control signal LD2 from the processor 52B to the light source apparatus 54 is inputted to the other of the two input terminals of the changeover switch 71. An output of the changeover switch 71 is supplied to the light source apparatus 54.

Where the processor 52A, which is a master processor, is connected to the endoscope 51A and operates as a simultaneous-type system, the processor 52A switches the changeover switch 71 so that a light source control signal from the processor 52A to the light source apparatus 54 is inputted to the changeover switch 71 and then outputted to the light source apparatus 54. Also, where the endoscope 51B is connected to the processor 52B and operates as a frame-sequential-type system, as indicated by the dotted line in FIG. 7, the processor 52A switches the changeover switch 71 so that a light source control signal from the processor 52B to the light source apparatus 4 is inputted to the changeover switch 71 and then outputted to the light source apparatus 54. The switching of the changeover switch 71 is performed via a switching control signal LDS from a control section in the processor 52A.

Note that here, since the simultaneous-type processor 52A is set as a master device, the no changeover switch 71 is provided in the frame-sequential-type processor 52B; however, a changeover switch 71 may also be provided in the processor 52B so that the frame-sequential-type processor 52B can be set as a master device.

Furthermore, where the endoscope system 1A is used as a simultaneous-type system, a user performs an operation on the master device, so the slave device may turn off lamps on an operation panel thereof. Accordingly, only lamps of operation switches and the like on an operation panel of the master device are on, and those on the operation panel of the slave device are off, which prevents a user from operating the slave device by mistake.

Still furthermore, in the endoscope system 1A constructed with "master" and "slave" set as described above, for operation-related apparatuses such as the keyboard 55 and a foot switch (not illustrated), those connected to the master processor are used. Accordingly, where the slave processor is used, also, an input and the like can be made via the keyboard connected to the master processor. In other words, an input device connected to a processor having a higher priority is enabled, and information inputted from the input device is transmitted to a processor with a lower priority.

(Operation)

Next, an operation of the system according to the present embodiment will be described, and processing for settings in the endoscope system 1A is the same as the processing in FIG. 3 and thus will be described using FIG. 3.

As illustrated in FIGS. 5 to 7, after the endoscope system 1A is constructed by connecting the processors 52A and 52B and the other apparatuses, first, master/slave setting processing is performed (S1). The processing in S1 is similar to the processing described in the first embodiment.

Here, it is assumed that a setting for determining the processor 52A as a master device and the processor 52B as a slave device is made. As described in the first embodiment, the master/slave setting is made via, e.g., a setting screen of each processor, the operation panel of each processor or a dedicated selection switch.

A master/slave setting is made for each of the two processors 52A and 52B, the processor that functions as a master device, here, the processor 52A set as "master" determines whether or not two processors 52A and 52B are correctly set as "master" and "slave", respectively (S2).

The determination is made by the processor 52A acquiring information on an operation mode of the processor 52B by means of communication with the processor 52B via the signal cable 57, which is the control wire CL1, and comparing the information with an operation mode thereof.

If the two processors are correctly set as "master" and "slave", respectively, that is, the operation mode of the processor 52B is set as "slave" and the operation mode of the master processor is set as "master" (S2: YES), the master processor transmits setting information pieces of its own to the slave processor (S3). Here, the processor 52A transmits the setting information pieces of its own to the processor 52B.

The setting information pieces transmitted in S3 is setting information pieces relating to video output settings such as aspect ratio and settings for connection with various peripheral devices connected to the master processor. Since the peripheral devices such as the monitor 53 are connected to the master processor, contents of settings for connections with the peripheral devices in the slave processor are made to agree with the settings for the peripheral devices in the master processor. Where the present system 1A that can be used for both the simultaneous method and the frame-sequential-type method is constructed using two processors 52A and 52B, it is necessary that settings in the processors 52A and 52B be at least partially in common If the two processors are not correctly set as "master" and "slave", for example, if the operation mode of the processor 52B and the operation mode of the master processor are both set as "master" (S2: NO), the setting information pieces for the master processor are not transmitted to the slave processor (S4) and the processing ends.

Upon the setting information pieces for the master processor being transmitted to the slave processor (S3), the slave processor updates setting information pieces of its own with the received setting information pieces of the master processor (S5). Here, the processor 52B updates the setting information pieces of its own with the corresponding setting information pieces from the processor 52A.

Note that here, although the slave processor updates the setting information pieces of its own for all of the setting information pieces received from the master processor, it is possible that the master processor transmits setting information pieces including a setting information piece for which an update is needed in the slave processor and the slave processor extracts only the setting information piece for which an update is needed from the received setting information pieces to perform a setting information update. In other words, the slave processor may select or extract a setting information piece in common with the master processor from the received setting information pieces to perform an update with only the setting in common with the setting content in the slave processor itself.

In other words, the processing in S5 provides a setting content changing section that changes a setting that is in common with a setting content in the slave processor from among received setting contents in the master processor (for example, settings such as a video output setting and/or a setting for connection with a peripheral device) to the received content in the master processor, in the slave processor.

When the endoscope system 1A constructed with "master" and "slave" set as described above is used as a simultaneous-type endoscope system, the endoscope 51A is connected to the processor 52A, whereby the endoscope system 1A can be used as a simultaneous-type endoscope system.

Where the endoscope 51A is connected to the processor 52A to use the endoscope system 1A as a simultaneous-type endoscope system, the processor 52A directly controls the peripheral devices connected thereto.

Note that when the endoscope system 1A is used as a simultaneous-type endoscope system, if the processor 52B is powered on, the processor 52B may turn off the lamps on the operation panel thereof.

Also, when the endoscope system 1A is used as a frame-sequential-type endoscope system, the endoscope 1B is connected to the processor 52B, whereby the endoscope system 1A can be used as a frame-sequential-type endoscope system.

Where the endoscope 51B is connected to the processor 52B to use the endoscope system 1A as a frame-sequential-type endoscope system, operation signals and control signals from the processor 52B are supplied to the respective peripheral devices including the monitor 53 and the light source apparatus 54 via the processor 52A, and the settings in the processor 52B that are in common with the processor 52A have been updated in S4, thus the peripheral devices connected to the master processor can be properly controlled and used.

Note that image quality settings in the monitor 53 may be switched according to whether the simultaneous method or the frame-sequential-type method is employed.

According to the endoscope system 1A constructed as described above, when the endoscope system 1A is used as a simultaneous-type endoscope system, the processor 52A set as a master processor controls the peripheral devices, and when the endoscope system 1A is used as a frame-sequential-type endoscope system, the master processor switches the connections with the keyboard, the monitor and the other peripheral devices so that the keyboard, the monitor and the other peripheral devices are connected to the slave processor, and the processor 52B set as a slave processor controls the peripheral devices via the master processor based on settings similar to those in the master processor.

As described above, the above-described embodiment eliminates the need to, when an endoscope system that can be used for both of the simultaneous method and the frame-sequential-type method is constructed using two processors, provide settings common to the two processors.

Accordingly, a user can use one endoscope system 1A as both of simultaneous-type and frame-sequential-type endoscope systems without, e.g., making re-settings in the peripheral devices that can be used in both the simultaneous method and the frame-sequential-type method, which have conventionally been made.

Various functions that each processor has in the above-described two embodiments will be described below. Note that the description of various functions will be provided below taking the first embodiment as an example, but can also be applied to the second embodiment.

(1) Display-Related Functions

Figure 8:
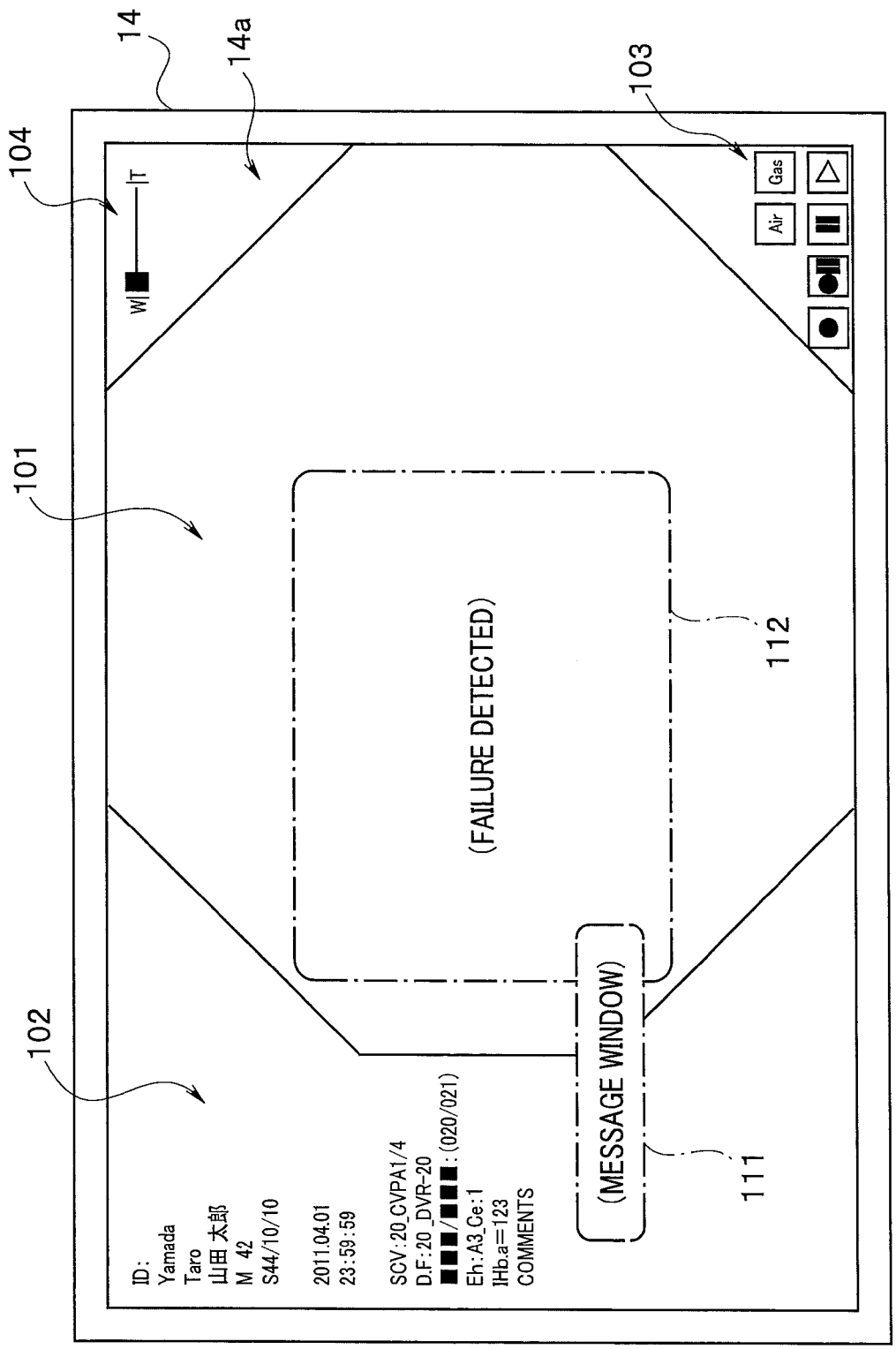
FIG. 8 is a diagram for describing display on a screen of a monitor 14.

FIG. 8 is a diagram for describing display on the screen of the monitor 14. As illustrated in FIG. 8, on the screen 14a of the monitor 14, various types of information can be displayed together with an endoscopic image. The screen 14a includes an octagonal endoscopic image display area 101 that displays an endoscopic image, an image information display area 102 that displays various types of information relating to an image, an operating state display area 103 that displays operating states of, e.g., peripheral devices, and a zooming state display area 104 that displays a zooming state.

In the endoscopic image display area 101, a video image of an object obtained as a result of image pickup by an image pickup apparatus in the endoscope.

In the image information display area 102, identification information (that is, ID) for a patient, which is the object, such as name, sex, age and birth date and information such as date and time of shooting are displayed.

Here, as illustrated in FIG. 8, the patient name is displayed in both of Chinese characters and English one-byte characters.

Also, a user can freely input comments and the inputted comments are displayed in the image information display area 102, a comment that is frequently inputted can be registered and a timing for inputting the registered comment can also be set. The timing for inputting a comment can be set according to a particular event. For example, a default comment such as the name of a hospital where the relevant image has been taken can be inputted as a comment at the timing of an event that is an examination end.

Also, in the image information display area 102, various types of information can be displayed, and each user can select and set information to be displayed for the user. Furthermore, settings can be made so that the display state is changed according to a predetermined event that has been set.

For example, it is possible that: at the time of preparation before start of an examination, all of display items are displayed, allowing a user to perform an input to each of all the items, but when an examination is started and an event that is an examination start is detected, only information selected by the user is displayed in the image information display area 102.

Accordingly, in the image information display area 102, various types of information can be displayed and a user can change information to be displayed or deleted according to a desired event.

In the operating state display area 103, operating states of, e.g., the processors and the peripheral devices are displayed in icons. FIG. 8 illustrates an example of display of icons for an image recording device and display of icons for pumps in the peripheral devices when an endoscopic image recorded in the image recording device is displayed. Although icons for functions such as replay, stop, pause and frame-by-frame advance for operation of the image recording device are displayed in FIG. 8, one of the icons, the function of the icon being operating, is displayed, enabling the user to check the operating state during the operation of the function. For the pumps, if a pump for, e.g., air feeding provided in the light source apparatus 17 is operating, an icon (Air) corresponding to such pump is displayed, and if a pump of a gas feeding apparatus is operating, an icon (Gas) corresponding to such pump is displayed. Although all of these icons are displayed in FIG. 8, only icons for functions or devices that are operating are displayed.

Note that for display of these icons displayed in the operating state display area 103, constant display or set-time period display can be selected and set. If the constant display is selected and set, an icon corresponding to a function or a pump that is operating is constantly displayed in the operating state display area 103. If the set-time period display is selected and set, an icon corresponding to a function or a pump that had a change in operation is displayed in the operating state display area 103 for a preset time period and disappears thereafter.

The zooming state display area 104 is displayed where an endoscope having a zoom function is connected, and in the zooming state display area 104, where a current zoom position is located between wide (W) and tele (T) is indicated by a position of a square icon.

Also, various functions can be assigned to a plurality of switches provided in the endoscope and one or more foot switches connected to, e.g., the processor, which are not illustrated, and in addition such assignment can be changed. Information indicating a function assigned to each switch can be displayed on the screen 14a so that a user can confirm the assigned functions of the respective switches. Various functions are assigned to various buttons in such a manner as described below, for example: a release button function is assigned to a switch 1 at the operation portion of the endoscope, an image recording button function is assigned to a switch 2 at the operation portion, and a print function is assigned to a foot switch 1. When the user performs, e.g., a predetermined key operation, a reference list on which the respective switches and the functions assigned thereto are associated with each other is displayed on the screen 14a. Accordingly, if the user wishes to confirm a function assigned to a switch, the user performs, i.e., the predetermined key operation, whereby the reference list is displayed for a time period determined in advance, enabling the user to confirm the function of each switch.

Still furthermore, a user can make specifications of the connected endoscope be displayed on the screen 14a to confirm the specifications. For example, if a user performs a predetermined operation of the keyboard 19, a window displaying information on the endoscope is displayed on the screen 14a. In the window, e.g., a model name, a serial number, a channel diameter, a distal end diameter and an insertion portion diameter of the endoscope are displayed, and along with the respective diameters, outer circumferential lengths of the respective parts are also displayed. This is because depending on the procedure, outer circumferential length display (in, for example, fr (French)) may be easier for a user to understand rather than diameter display (in, for example, mm (millimeters)).

(2) Message-Related Functions

On the screen 14, various types of messages can be displayed. Examples of the message include an error message. In FIG. 8, as indicated by the alternate long and short dash line, a predetermined message window 111 appears on the screen 14a and displays a message such as an error message.

Predetermined priorities are set for the messages. The number of message windows 111 is determined in advance, and if the number of messages to be displayed exceeds the number determined in advance, only such determined number of messages having higher priorities can be displayed. Therefore, if a plurality of messages are generated, a message having a highest priority is displayed, and messages having priorities lower than that are not displayed behind the respective messages having the higher priorities. In other words, a message window 111 having a higher priority is displayed with the message window 111 superimposed on a message window 111 having a lower priority. Then, display control is performed so that, for example, if a cause for an error corresponding to the message having the highest priority is removed, the message window 111 corresponding to the error message disappears, and a message window 111 for a message having a second highest priority appears.

In a message window 111, an error message for erroneous connection of a peripheral device is also displayed. A plurality of peripheral devices are connected to the master processor, and a plurality of connectors of same type exist in the master processor. For example, there are a plurality of connectors conforming to common standards such as USB (universal serial bus), a user may connect a peripheral device to a wrong connector.

Therefore, when the peripheral devices are connected to the respective connectors, the master processor communicates with the peripheral devices to acquire information on types of the peripheral devices and thereby checks whether or not a correct peripheral device is connected to each connector, and if a wrong peripheral device is connected, makes an error message window 111 be displayed on the screen 14a to provide a warning to the user.

(3) Peripheral Device Control Function

Since various peripheral devices can be connected to the master processor in the endoscope system 1, the light source apparatus 17 may include a pump for air feeding and the gas feeding apparatus for feeding carbon dioxide into a body may be connected to the master processor. If the pump for air feeding in the light source apparatus 17 operates during the gas feeding apparatus operating, the carbon dioxide concentration in the body cavity may decrease, and in order to perform control to prevent such decrease in carbon dioxide concentration, exclusion control is performed for the pump in the light source apparatus 17 and the pump in the gas feeding apparatus. Control to consider a later instruction as effective is performed as follows: If a user provides an instruction to turn on the pump in the gas feeding apparatus after the user provides an instruction to turn on the pump in the light source apparatus 17, the master processor considers the latter instruction as effective, and stops the pump in the light source apparatus 17 and turns on the pump in the gas feeding apparatus. As described above, a pump in operation is displayed in an icon on the screen 14a.

Furthermore, each processor has a function that stores information on an endoscope connected thereto. In other words, each processor records information on a history of endoscope connections in a non-volatile memory as log data.

Also, in each peripheral device, operation log data of its own is recorded, and thus, the master processor has a function that collects log data of the plurality of peripheral devices connected thereto and transmits the log data to the server 41.

Also, if the peripheral devices also have a clock function, the master processor transmits time information to the respective peripheral devices so as to adjust the clocks of the respective peripheral devices to the clock of its own.

Also, a key for operating a particular function of a particular peripheral device may be provided in the keyboard 19. For example, a dedicated key for enabling a PIP (picture-in-picture) function or a POP (picture-out-picture) function in the monitor 14 and/or a selection switch for a channel displayed on the monitor 14 are provided in the keyboard 19. Consequently, a user can operate a peripheral device via the keyboard 19 without directly operating the peripheral device.

Furthermore, in the master processor, not only the connectors are connected one by one to the peripheral devices, but also a plurality of peripheral devices may be connected in series to one connector. In such case, if a plurality of apparatuses having the same function are connected to one connector, the master processor provides error message display. For example, if a plurality of image recording devices are connected to one connector, the master processor can control only one image recording device, and thus in such case, an error message such as described above is displayed.

Also, in the cases where the endoscope system 1 cannot normally operate such as endoscope failures and processor failures, as indicated by the alternate long and short dash line in FIG. 8, the master processor makes a window 112 for failure indication, the window 112 covering a large part of the screen 14a, be displayed on the screen to notify a user of detection of a failure.

Also, the master processor can make a list of apparatuses included in the endoscope system 1 be displayed according to a predetermined operation. For example, when a user performs a predetermined operation of the keyboard 19, a window indicating, e.g., type information and/or manufacturer number of, e.g., the processors, the light source apparatus, the endoscope, the printer and the image recording device in a list form is displayed on the screen 14a as system configuration information.

Also, settings for the peripheral devices can be made on the setting screen of the master processor. Consequently, a user does not need to make a setting screen for each peripheral device be displayed on the monitor 14 to make settings for the peripheral device. Since items of settings for the peripheral devices are included in the setting screen of the master processor, the user can make settings for each peripheral device using the setting screen.

The master processor can also record a still image, and can make the recorded still image be recorded in an external memory. Examples of the external memory include a USB memory, and there may be cases that data cannot correctly be written to the external memory. Therefore, the master processor has a simple check function for an external memory connected thereto.

Here, the master processor performs processing steps of writing test data to an external memory and then reading the test data to check if the test data can correctly be read, and further deleting the written data and then checking if the data is correctly deleted, whereby the simple check function for external memory is provided.

(4) Setting-Related Functions

The master processor has a function that stores contents of settings in the master processor itself and the peripheral devices in an external memory such as a USB memory. Furthermore, the master processor also has a function that reflects contents of settings recorded in the external memory in the settings in the master processor itself and the peripheral devices.

Accordingly, a user can use contents set in a certain system for another endoscope system without the need to input previously-set contents again.

Also, for security reasons, a setting screen is not displayed unless a user inputs his/her ID and a password in order to display the setting screen. Although there are various types of setting screens, if a user attempts to make a setting screen that needs to be secured be displayed, the user is requested to input his/her ID and a password, and if the user is correctly authenticated, the setting screen is displayed.

Note that when a setting screen list for activating various setting screens is displayed, a user may be required to input an ID and a password.

Also, as illustrated in FIG. 8, when a birth date of a patient is displayed, a code for an era name is displayed, and in each processor, a new era name can be set and registered.

Also, a user can perform a predetermined operation without operating the keyboard. For example, if a user performs a predetermined operation of the master processor, a plurality of operation function buttons are displayed on the screen 14a. A selection cursor can be moved among the respective buttons displayed on the screen via up, down, left and right arrow keys on a front panel of the processor, and if a user operates an enter key on the front panel when a desired function button is selected, the selected function is executed. Accordingly, the user can provide an instruction for a desired operation to the master processor and various devices without using the keyboard 19.

(5) Still Image Recording Function

Furthermore, on the front panel of a processor, an "examination" button is provided, and a user can provide a trigger for an examination start and a trigger for an examination end to the processor. Upon the "examination" button being pressed, an examination is started, LED lamps on the front panel and the keyboard are turned on to indicate that an examination is underway, and upon the "examination" button being pressed again, which provides a trigger for an examination end, the LED lamps on the front panel and the keyboard are turned off.

Furthermore, the processor can disable the "examination" button by a setting.

Note that in case that a user forgets to press the "examination" button to provide a trigger for an examination start, when it is detected that an instruction to record a still image or a moving image is provided first, such instruction serves as a trigger for an examination start.

Still furthermore, in case that a user forgets to provide a trigger for an examination end, the user can make a setting in the processor so that detection of power-off of the processor or removal of the endoscope serves as a trigger for an examination end.

Accordingly, where the function of the "examination" button is set to be enabled, if, e.g., the processor is powered off without provision of a trigger for an examination end, the last examination is considered as being ended when the processor is turned on next.

Also, likewise, if an attempt to change patient information is made during an examination, a user is urged to confirm if the ongoing examination ends on the screen. Accordingly, the user can make a setting in the processor so that the ongoing examination ends when such confirmation is made.

Furthermore, the processor records a still image in an internal memory, and even if the internal memory has no free space, a recording operation is not stopped and recording can be made on a peripheral device such as a printer.

Still furthermore, the endoscope is provided with a dedicated button for recording information such as a flag indicating that an image to be recorded or a recorded image is an important image. For example, a release button for ordinary recording and a second release button for also recording that the relevant image is an important image are provided at the operation portion of the endoscope, enabling a user to know whether or not the relevant image is an important image after the examination. Note that the dedicated button may be provided in a processor.

(6) Output Function for PC

Each processor includes an output terminal for an output to a monitor of a personal computer (hereinafter referred to as PC). Thus, each processor performs an interlace/progressive conversion (hereinafter referred to as I/P conversion) that converts an interlaced video signal to a progressive video signal as well as a frame rate conversion, and for reduction of sizes of processing circuits for the two conversions to reduce a delay in processing, the two conversions are performed using one memory.

Figure 9:
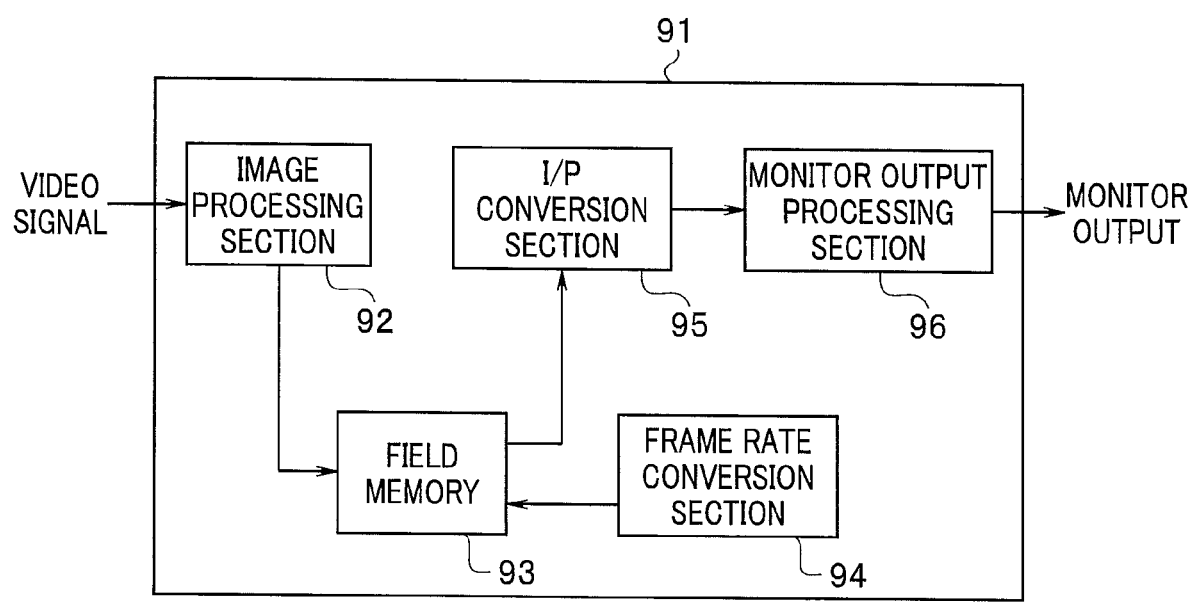
FIG. 9 is a block diagram illustrating a configuration of an image processor included in each processor.

FIG. 9 is a block diagram illustrating a configuration of an image processor included in each processor. The image processor 91 includes an image processing section 92 that receives an input of a digital video signal, a field memory 93, a frame rate conversion section 94, an I/P conversion section 95 and a monitor output processing section 96.

The image processing section 92 controls writing of an inputted video signal to the field memory 93, and the frame rate conversion section 94 controls a timing for reading the video signal written in the field memory 93. The I/P conversion section 95 generates a progressive video signal based on the video signal from the field memory 93 to perform an I/P conversion.

More specifically, in the field memory 93, video signals for odd-numbered fields and video signals for even-numbered fields are stored, and the frame rate conversion section 94 controls timings for reading the video signals for odd-numbered fields and the video signals for even-numbered fields stored in the field memory 93, whereby a difference in frequency between an input frame rate and an output frame rate is compensated.

The I/P conversion section 95 generates a progressive video signal from video signals for a latest odd-numbered field and an even-numbered field one field before the latest field or video signals for a latest even-numbered field and an odd-numbered field one field before the latest field, which have been read during the same frame output period, and outputs the progressive video signal to the monitor output processing section 96.

If the output frame rate is higher than the input frame rate, a video signal for the same field is outputted twice to compensate a difference in frequency. Also, if the output frame rate is lower than the input frame rate, a video signal for a field that is not outputted is provided to compensate a difference in frequency.

Furthermore, when the I/P conversion section 95 generates one output frame from video signals for two fields, the I/P conversion section 95 performs, for example, median filtering using a method according to three-point median to generate a video signal for the output frame.

Note that the I/P conversion section 95 may be configured to perform, e.g., filtering switched according to an amount of movement and/or combining processing using interpolation instead of a median filter.

As described above, a frame rate conversion and an I/P conversion are performed using a common field memory, enabling downsizing of the processing circuits and reduction in processing delay.

Each of the embodiments described above enables provision of a medical device system that eliminates the need to, when two medical devices are used in combination, make settings common to the medical devices.

The present invention is not limited to the above-described embodiments and various modifications, alterations and the like are possible without departing from the spirit of the present invention.

What is claimed is:

1. An endoscope system in which a first processor and a second processor are connected in such a manner that the first processor and the second processor can communicate with each other, the endoscope system comprising:
    a first image pickup device that picks up an image of an inside of a body cavity and outputs a first image pickup signal;
    a first processor that processes the first image pickup signal from the first image pickup device and outputs a first image signal, and transmits a first setting content that is set, via communication;
    a second image pickup device that picks up an image of the inside of the body cavity and outputs a second image pickup signal;
    a second processor that processes the second image pickup signal from the second image pickup device and outputs a second image signal, and changes a common setting content based on the setting content received from the first processor via communication, the second processor having a priority determined to be lower than that of the first processor;
    a three-dimensional image generation apparatus that generates a three-dimensional image from the first image signal and the second image signal; and
    an operation device via which an operational instruction for the first processor is inputted,
    wherein upon an input of an operational instruction for still image display via the operation device, the first processor makes a setting for or provides an instruction to the three-dimensional image generation apparatus so as to output only the first image signal.

2. The endoscope system according to claim 1, wherein the first image pickup device and the second image pickup device are provided in an endoscope.

3. The endoscope system according to claim 1, wherein the setting content includes information relating to an image quality setting and a video output setting.

4. The endoscope system according to claim 1, wherein the second processor changes the common setting content by extracting only information necessary for update from the received setting content from the first processor to update the common setting content.

5. The endoscope system according to claim 1, wherein the second processor turns off a lamp on an operation panel thereof after the change of the setting content.

* * * * *